US008928876B2

(12) United States Patent
Chan et al.

(10) Patent No.: US 8,928,876 B2
(45) Date of Patent: Jan. 6, 2015

(54) CELL COUNTING AND SAMPLE CHAMBER AND METHODS OF FABRICATION

(75) Inventors: Leo L. Chan, North Andover, MA (US); Jean Qiu, North Andover, MA (US)

(73) Assignee: Nexcelom Bioscience LLC, Lawrence, MA (US)

( * ) Notice: Subject to any disclaimer, the term of this patent is extended or adjusted under 35 U.S.C. 154(b) by 82 days.

(21) Appl. No.: 13/519,283

(22) PCT Filed: Jan. 19, 2011

(86) PCT No.: PCT/US2011/021676
§ 371 (c)(1),
(2), (4) Date: Jan. 3, 2013

(87) PCT Pub. No.: WO2011/091007
PCT Pub. Date: Jul. 28, 2011

(65) Prior Publication Data
US 2013/0120747 A1  May 16, 2013

Related U.S. Application Data

(60) Provisional application No. 61/296,778, filed on Jan. 20, 2010.

(51) Int. Cl.
| G01N 1/10 | (2006.01) |
| G01N 21/03 | (2006.01) |
| B01L 3/00 | (2006.01) |
| B29C 65/50 | (2006.01) |
| B29C 65/00 | (2006.01) |
| G01N 15/14 | (2006.01) |
| G01N 21/64 | (2006.01) |
| B29L 31/00 | (2006.01) |
| B29C 65/48 | (2006.01) |

(52) U.S. Cl.
CPC ......... *G01N 21/03* (2013.01); *B01L 3/502707* (2013.01); *B29C 65/5057* (2013.01); *B29C 66/1122* (2013.01); *B29C 66/53461* (2013.01); *G01N 15/1463* (2013.01); *G01N 15/1484* (2013.01); *G01N 21/6458* (2013.01); *B01L 2200/0689* (2013.01); *B01L 2300/0877* (2013.01); *B01L 2300/0887* (2013.01); *B29C 66/71* (2013.01); *B29L 2031/756* (2013.01); *B29C 65/5021* (2013.01); *B29C 65/4825* (2013.01); *B29C 65/4835* (2013.01)
USPC .......................................................... 356/246

(58) Field of Classification Search
CPC ... G01N 21/05; G01N 21/03; G01N 21/0303; G01N 30/74; G01N 21/031
USPC .......................................................... 356/246
See application file for complete search history.

(56) References Cited

U.S. PATENT DOCUMENTS

| 4,690,503 | A | * | 9/1987 | Janssen et al. | 385/128 |
| 4,761,381 | A | * | 8/1988 | Blatt et al. | 436/165 |
| 6,558,630 | B1 | * | 5/2003 | Degn et al. | 422/501 |
| 2004/0145805 | A1 | * | 7/2004 | Qiu | 359/398 |
| 2005/0136260 | A1 | * | 6/2005 | Garcia | 428/411.1 |
| 2009/0062152 | A1 | * | 3/2009 | Linton et al. | 506/39 |

* cited by examiner

*Primary Examiner* — Abdullahi Nur
*Assistant Examiner* — Md Rahman
(74) *Attorney, Agent, or Firm* — Milstein Zhang & Wu LLC

(57) ABSTRACT

The invention generally relates to analytical and monitoring systems useful for analyzing and measuring cells and biological sample. More particularly, the invention relates to a unique cell counting chamber, e.g., a thin gap fluidic cell chamber for both bright field and fluorescent imaging of bacteria or parasites, and methods for making the same.

14 Claims, 18 Drawing Sheets

Bright field of 20 um chamber 10 ms   FL image of beads at 20 ms

FL of bacteria and Yeast right after mixing SYTO 9

CELL COUNTING AND SAMPLE CHAMBER AND METHODS OF FABRICATION

PRIORITY CLAIMS

This application is the national phase of PCT/US11/21676, filed Jan. 19, 2011, which claims the benefit of priority from U.S. Provisional Application Ser. No. 61/296,778, filed Jan. 20, 2010, the entire content of each of which is incorporated herein by reference for all purposes.

TECHNICAL FIELDS OF THE INVENTION

The invention generally relates to analytical and monitoring systems useful for analyzing and measuring cells and biological sample. More particularly, the invention relates to a unique sample chamber, e.g., a thin gap fluidic cell counting chamber useful for both bright field and fluorescent imaging of bacteria or parasites, and methods for making and using the same.

BACKGROUND OF THE INVENTION

Detection, identification, quantification, and characterization of biomolecules or cells of interest through testing of biological samples is an important aspect in the fields of medical diagnostics and biomedical research. Biological solutions, such as blood, spinal fluid, cell culture and urine, are routinely analyzed for their microscopic particle concentrations.

Existing bacteria cell counting methods include inexpensive but manual cell counting hemacytometer and expensive large instruments such as flow cytometer, plate reader, as well as bacterial colony measurement. The manual cell counting device is extremely tedious and inconsistent and is prone to human errors and cleaning procedures. Flow cytometry requires large quantity of samples, due to the utilization of lasers, is very expensive and requires well-trained professionals to perform the instrument in order to obtain accurate results. Bacteria colony and measurement by optical density has also been used in cell counting, but the preparation is tedious and prone to contamination. In addition, it requires days and even weeks for the bacteria culture to be accurately measurable.

Recently, an automated cell counting instrument has been developed by Nexcelom Bioscience that utilizes a microfluidic counting chamber, which can automatically count cells larger than 2 μm in diameter.

There is, however, a pressing need for efficient and consistent imaging and counting instrument and methods for biological particles with diameters less than 2 μm, such as bacteria or parasites.

SUMMARY OF THE INVENTION

The invention is based, in part, on the discovery of a novel thin gap fluidic chamber design and efficient and cost-effective methods of fabrication and manufacture. In order to consistently image and count the particles, a thin gap fluidic sample chamber is required to minimize the effect of multiple imagine planes. Depending on the particles sizes, the novel fabrication method can be used to create the appropriate chamber gap height. The cell chamber of the invention can be used for both bright field and fluorescent imaging of bacteria, parasites, protein aggregates, or larger mammalian, insect, or plant cell types.

In one aspect, the invention generally relates to a sample chamber suitable for holding a liquid sample for optical imaging. The sample chamber includes: a top layer; an adhesive layer; a bottom layer; a sample holding cavity between the adhesive layer and the bottom layer having a fixed depth of from about 0.5 μm to about 1,000 μm; and an assess port for placing a sample into or out of the chamber; wherein at least a portion of the adhesive layer is optically clear in the range of about 250 nm to about 10,000 nm in wavelength, and wherein at least a portion of the top layer and the bottom layer is optically clear in the range of about 300 nm and about 10,000 nm in wavelength.

The bottom layer of the sample chamber further includes a base film.

In certain embodiments, the sample holding cavity of the sample chamber has a fixed depth of from about 1 μm to about 100 μm. In certain preferred embodiments, the sample holding cavity has a fixed depth of from about 2 μm to about 50 μm. In certain preferred embodiments, the sample holding cavity has a fixed depth of from about 2 μm to about 20 μm. In certain other preferred embodiments, the sample holding cavity has a fixed depth less than about 2 μm. In certain other preferred embodiments, the sample holding cavity has a fixed depth less than about 1 μm.

In some embodiments, at least a portion of the adhesive layer is optically clear in the range of about 300 nm to about 10,000 nm in wavelength, and wherein at least a portion of the top and the bottom layers is optically clear in the range of about 300 nm and about 10,000 nm in wavelength.

The top layer of the sample chamber may be made of a material selected from the group consisting of polyester, polycarbonate, poly(methyl methacrylate) (or PMMA), polystyrene and cyclic olefin copolymer, and other optically clear plastic films.

The adhesive layer of the sample chamber may be a pressure-sensitive adhesive layer that includes a material selected from acrylic or acrylate adhesive.

The bottom layer may include an irradiation or thermally cured material. For example, the bottom layer may be a UV-cured polymeric material. In certain preferred embodiments, the UV-cured materials are selected from the group consisting of UV-cured acrylate, urethane and epoxy.

In certain preferred embodiments, the sample chamber further includes a backing layer that is bond to the bottom layer. The backing layer may include a material selected from the group consisting of polyester, polycarbonate, PMMA, polystyrene and cyclic olefin copolymer, and other optically clear plastic films.

In another aspect, the invention generally relates to a sample chamber suitable for holding a biological sample for optical imaging. The sample chamber includes: an optically clear bottom layer; an optically clear top layer; an optically clear adhesive layer binding the top layer on one side and forming a sample holding chamber on the other side with an irradiation- or thermally-cured polymer layer, wherein the sample holding chamber having a fixed depth from the adhesive layer to the irradiation- or thermally-cured polymer layer of from about 0.5 μm to about 1,000 μm; an inlet port for introducing a sample into the chamber; and an outlet port for removing a sample from the chamber (the sample holding cavity).

In some embodiments, the sample holding chamber has a fixed depth of from about 1 μm to about 100 μm. In certain preferred embodiments, the sample holding chamber has a fixed depth of from about 2 μm to about 50 μm. In certain preferred embodiments, the sample holding chamber has a fixed depth of from about 2 μm to about 20 μm. In certain other preferred embodiments, the sample holding chamber has a fixed depth of less than about 2 µm. In certain other preferred embodiments, the sample holding chamber has a fixed depth of less than about 1 µm.

For some applications, it is preferred that at least a portion of the adhesive layer is optically clear in the range of about 250 nm to about 10,000 nm in wavelength.

The top layer may be made of a material selected from the group consisting of polyester, polycarbonate, PMMA, polystyrene and cyclic olefin copolymer.

The adhesive layer may be a pressure-sensitive adhesive layer comprising a material selected from acrylic or acrylate adhesive.

The bottom layer may include an irradiation or thermally cured material. In certain preferred embodiments, the bottom layer comprises a UV-cured polymeric material, for example, a material selected from the group consisting of acrylate, urethane and epoxy.

In certain preferred embodiments, the sample chamber further includes a backing layer that is bond to the bottom layer. The backing layer may be made of a material selected from the group consisting of polyester, polycarbonate, PMMA, polystyrene and cyclic olefin copolymer.

In yet another aspect, the invention generally relates to a method for fabricating a sample chamber. The method includes: providing an optically clear backing layer; placing uniformly an irradiation- or thermally-curable layer on the backing layer; imprinting a preformed structure mold on to the irradiation- or thermally-curable layer, wherein the preformed structured mold protruding into the irradiation- or thermal-curable layer; curing the irradiation- or thermally-curable layer by irradiation or thermal treatment; removing the preformed structure mold, thereby forming an imprinted structure in the irradiation- or thermal-cured layer reflecting the preformed structure of the mold; and placing an optically clear top film having an optically clear adhesive layer on to the imprinted structure of the irradiation- or thermally-cured layer, thereby forming a chamber having the imprinted structure.

The method may further include: forming one or more access port on the chamber allowing introduction and removal of a sample.

The optically clear backing layer is made of a material selected from the group consisting of polyester, polycarbonate, PMMA, polystyrene and cyclic olefin copolymer.

The irradiation layer may be made of an UV-curable material selected from the group consisting of UV-cured acrylate, urethane and epoxy.

The optically clear top film is made of a material selected from the group consisting of polyester, polycarbonate, PMMA, polystyrene and cyclic olefin copolymer.

In some preferred embodiments, the preformed structure mold is formed from aluminum mold.

In yet another aspect, the invention generally relates to a method for manufacturing a sample chamber suitable for holding a biological sample. The method includes: imprinting a preformed structure mold on to an irradiation- or thermal-curable layer, the preformed structured mold protruding into the irradiation- or thermal-curable layer; curing the irradiation- or thermal-curable layer to form an optically clear layer thereby forming a chamber having the imprinted structure; removing the preformed structure mold; binding an optically clear top film to the imprinted structure of the irradiation- or thermal-cured layer, thereby forming a sample chamber; and forming one or more access port on the chamber allowing introduction and removal of a sample.

Thus, in yet another aspect, the invention generally relates to a method for manufacturing a sample chamber suitable for holding a biological sample. The method includes: imprinting a preformed structure mold on to a melt plastic layer; cooling the melt plastic layer resulting an imprinted structure thereon; removing the preformed structure mold; binding an optically clear top film to the imprinted structure, thereby forming a sample chamber; and forming one or more access port on the chamber allowing introduction and removal of a sample.

In yet another aspect, the invention generally relates to a method for manufacturing a sample chamber suitable for holding a biological sample. The method includes: stamping a hot preformed structure mold on to a plastic layer, resulting an imprinted structure thereon; removing the preformed structure mold; cooling the plastic layer; binding an optically clear top film to the imprinted structure, thereby forming a sample chamber; and forming one or more access port on the chamber allowing introduction and removal of a sample.

DETAILED DESCRIPTION OF THE INVENTION

The invention is based, in part, on the discovery of unique sample chamber designs and efficient and cost-effective fabrication and manufacturing methods that allow accurate, consistent and efficient imaging of bacteria or parasites using both bright field and fluorescent.

Bacteria have a wide diversity of shapes and sizes. Bacterial cells typically are about one tenth the size of eukaryotic cells and are typically 0.3-5.0 micrometres in length. Among the smallest bacteria are members of the genus *Mycoplasma*, which measure only 0.3 micrometres, as small as the largest viruses. Some bacteria may be even smaller. Most bacterial species are either spherical or rod-shaped although other shapes do exist. Many bacterial species exist simply as single cells, others associate in characteristic patterns such as pairs, chains, and clusters. Bacteria can also be elongated to form filaments.

When bacteria form a parasitic association with other organisms, they become pathogens. Pathogenic bacteria are a major cause of human death and disease and cause various infections such as tetanus, typhoid fever, diphtheria, syphilis, cholera, foodborne illness, leprosy and tuberculosis.

Figure 1:
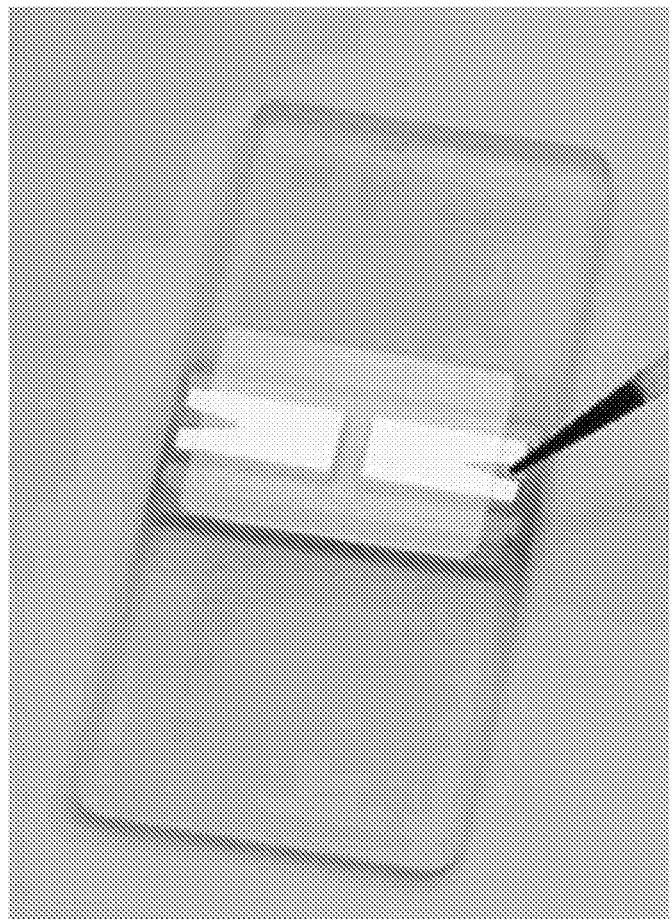
FIG. 1 depicts a traditional manual bacteria hemacytometer (Cole Palmer).

Bacteria and parasites have been imaged using manual cell counting hemacytometer, flow cytometer, plate reader, as well as various fluorescent and electron microscopy and atomic force microscopy. One example is the traditional method of manual cell counting as exemplified by the bacteria hemacytometer of Cole Palmer (FIG. 1). It uses capillary action to distribute cells into an H-shaped moat that forms two counting areas with enhanced Neubauer rulings. An V-slash at loading side provides fluid loading. When viewed through a microscope, hemacytometers display white Neubauer markings against a dark background. Cover slips cover moat region 0.1 mm above ruled surface.

More recently, certain instruments have been developed that are useful for imaging and counting cells and biological materials including certain bacteria and parasites. An example is an instrument developed by Nexcelom Bioscience (Cellometer Vision 10X), which is an automated cell counting instrument that utilizes a microfluidic counting chamber and can automatically count cells larger than 2 μm in diameter.

A significant limitation of the existing instruments and methods is that none of them provide automatic sample imaging and cell counting that are efficient and provide accurate and consistent results while at the same time are cost-effective. A major reason for this limitation has been the lack of an enabling sample (or cell) chamber design and corresponding efficient and low cost fabrication and manufacturing methods.

The present invention provides sample chamber designs and fabrication methods that allow efficient and effective imaging of small size biological particles such bacteria or parasites using both bright field and fluorescent.

Figure 2:
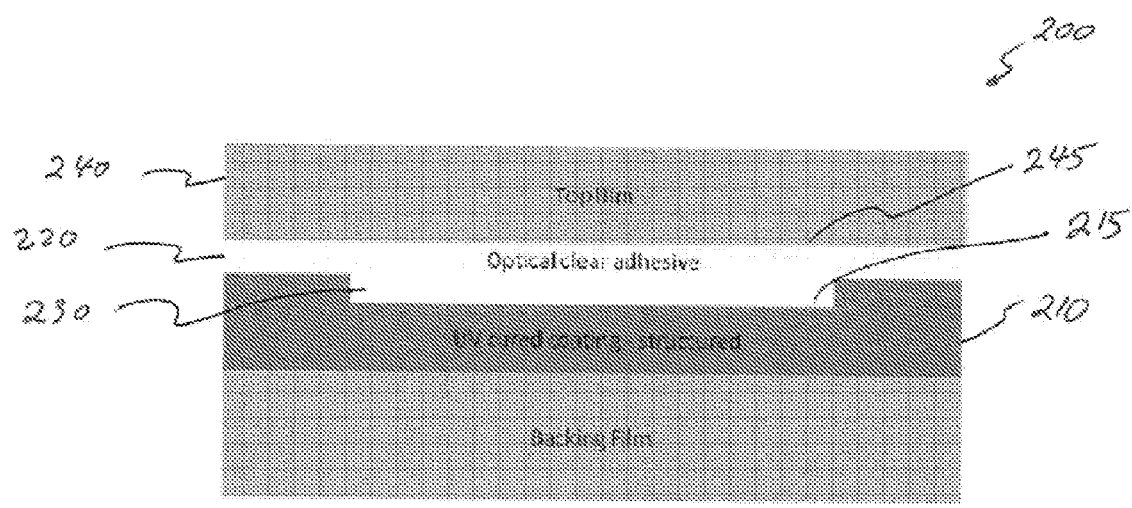
FIG. 2 depicts a schematic cross-section of an exemplary sample chamber according to an embodiment of this invention.
Figure 3:
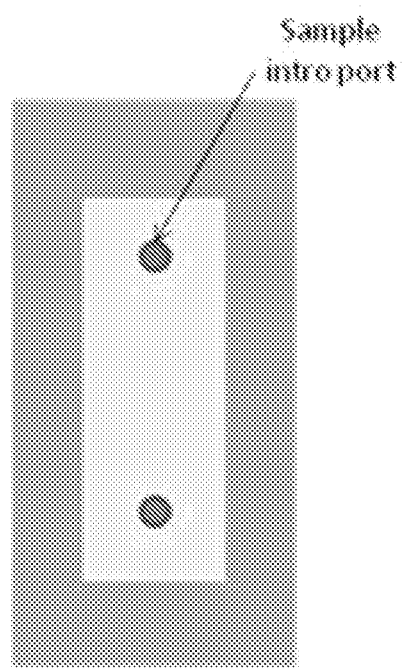
FIG. 3 depicts a schematic top view of an exemplary sample chamber according to an embodiment of this invention.

Referring to FIG. 2, which illustrates the cross section of a cell counting chamber according to an embodiment of this invention. The cell counting chamber 200 has a bottom layer 210, which may be a layer of a UV-cured material. On the bottom layer 210, certain pre-designed cavity 230 is present (profiled on the top surface 215 of the bottom layer 210). An optically clear adhesive layer 220 is placed between the bottom layer 210 and a top layer 240, bonding the top surface 215 of the bottom layer 210 and the bottom surface 245 of the top layer 240 (with the exception where the pre-designed cavity 230 is present). Additionally, at least one (and preferably two FIG. 3) sample port (e.g., a circular-shaped opening) is present allowing access to the cavity 230.

Figure 4:
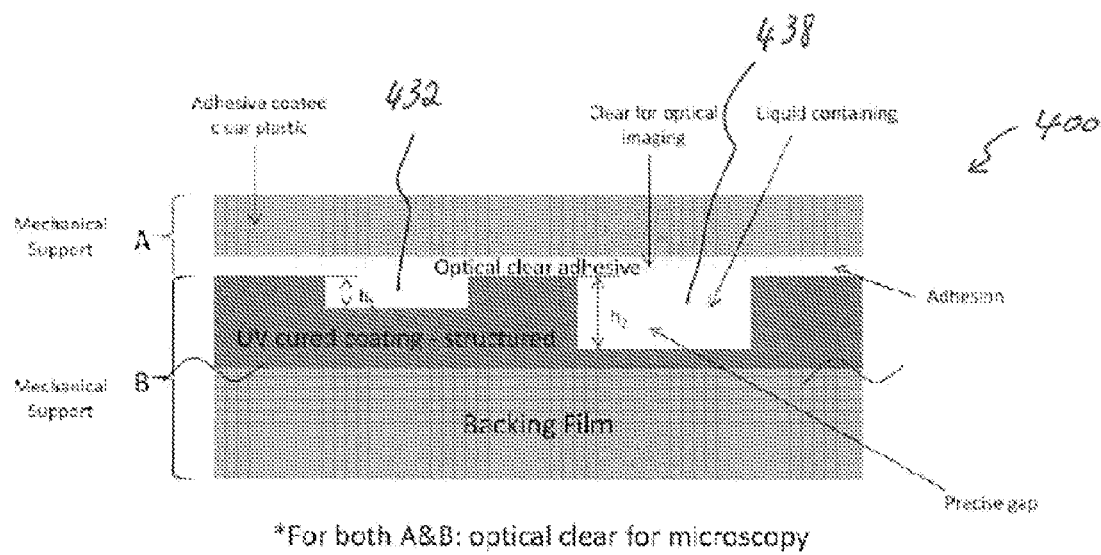
FIG. 4 depicts a schematic cross-section of an exemplary sample chamber according to an embodiment of this invention.
Figure 5:
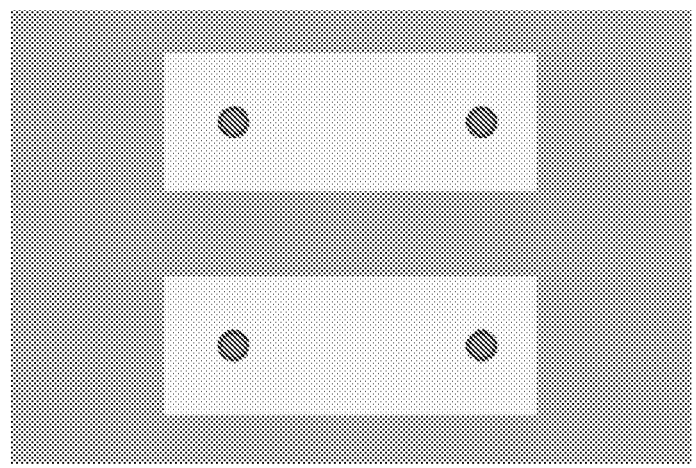
FIG. 5 depicts a schematic top view of an exemplary sample chamber according to an embodiment of this invention.

Referring to FIG. 4, which depicts a cross section of another exemplary embodiment of the present invention. Here, sample chamber 400 has two sample holding cavities, 432 and 438 with fixed heights $h_1$ and $h_2$, respectively. The fixed heights $h_1$ and $h_2$ may be identical or different. The corresponding sample ports (FIG. 5) allow introduction of samples to the two cavities individually, therefore enabling side-by-side imaging of two different samples.

In order to develop a fabrication method that is cost effective and efficient for imaging cytometry, a very important issue has to be addressed, i.e., the enclosure of the counting chamber. The chamber depth could be fabricated in various ways, but the most efficient method as disclosed herein employs imprint lithography. This method utilizes a mold that, when imprinted with a thermally or light cured solution, forms a pre-designed structure on a plastic sheet. To avoid expensive equipments and multiple steps, a unique method as disclosed herein utilizes an optical clear adhesive to cover the entire top surface that provides clear imaging capability while enclosing the chamber.

Figure 6:
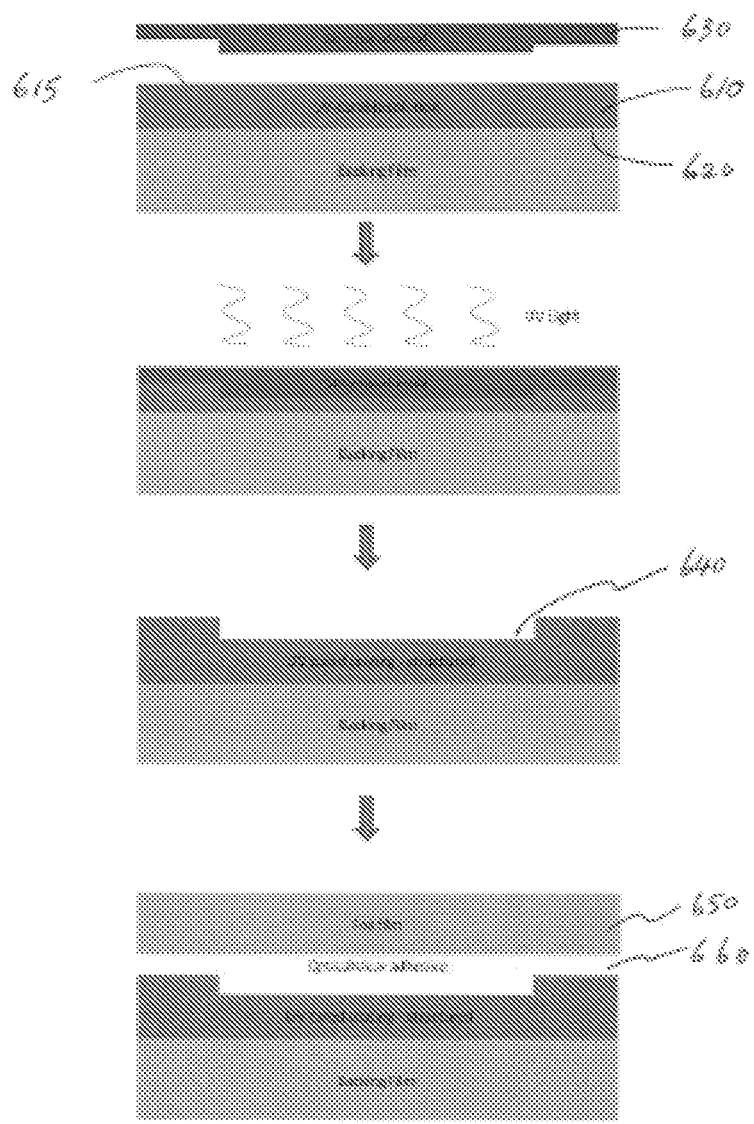
FIG. 6 is a schematic depiction of a fabrication method.

FIG. 6 depicts an exemplary embodiment of a fabrication method according to this invention. A UV-curable solution 610 is dispensed over a plastic surface 620 and a structure mold 630 is imprinted on the surface 615 of the solution 610. UV light is allowed to cure the solution 610. The mold 630 is removed and the desired cavity structure 640 is formed. Then, a top layer 650 with an adhesive layer 660 is placed on top of the UV-cured layer 610 with structure 640.

An important aspect of the invention lies in the utilization of optically clear transfer adhesive as the enclosing layer of the thin gap chamber, which simplified the method from using an expensive and tedious ink transfer system or adhesive coating to simply laying down a top sheet to form the chamber enclosure on the molded structure.

Figure 7:
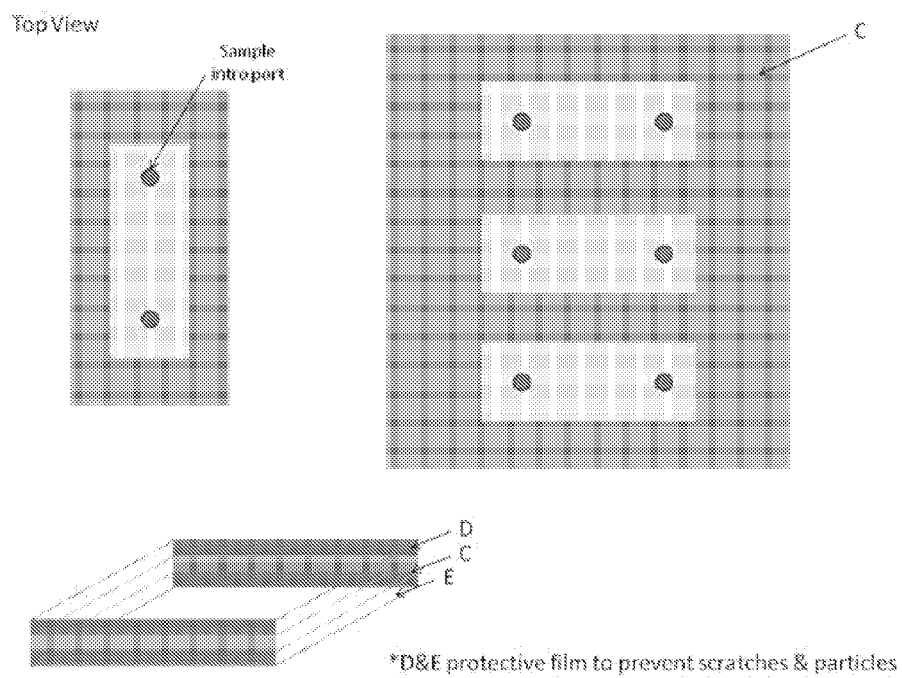
FIG. 7 depicts an aspect of an exemplary fabrication method according to the invention.
Figure 8:
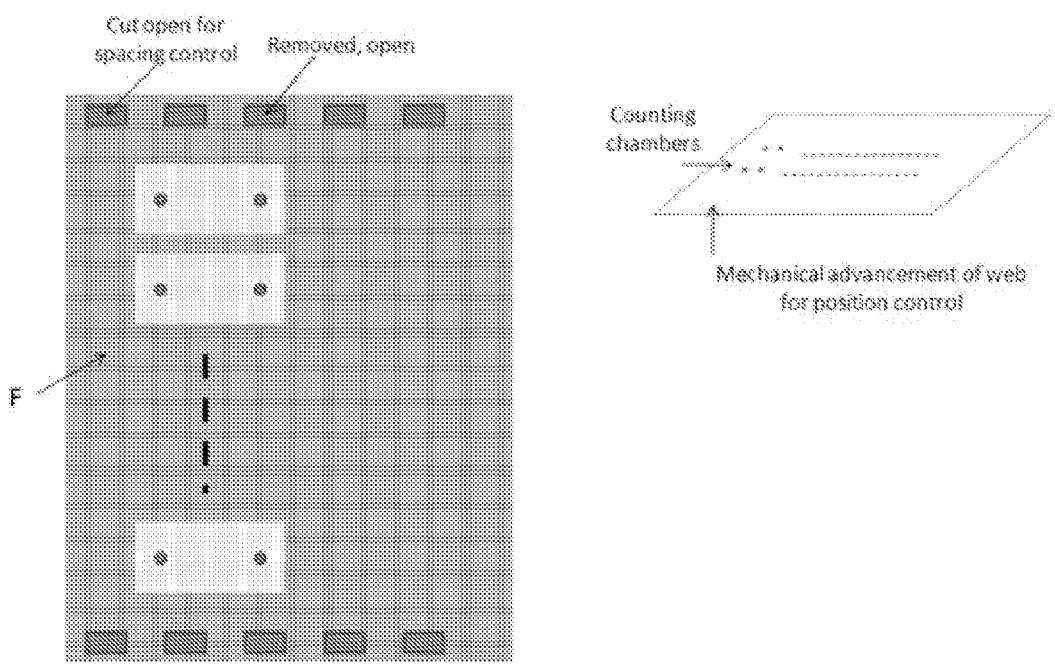
FIG. 8 depicts an aspect of an exemplary fabrication method according to the invention.
Figure 9:
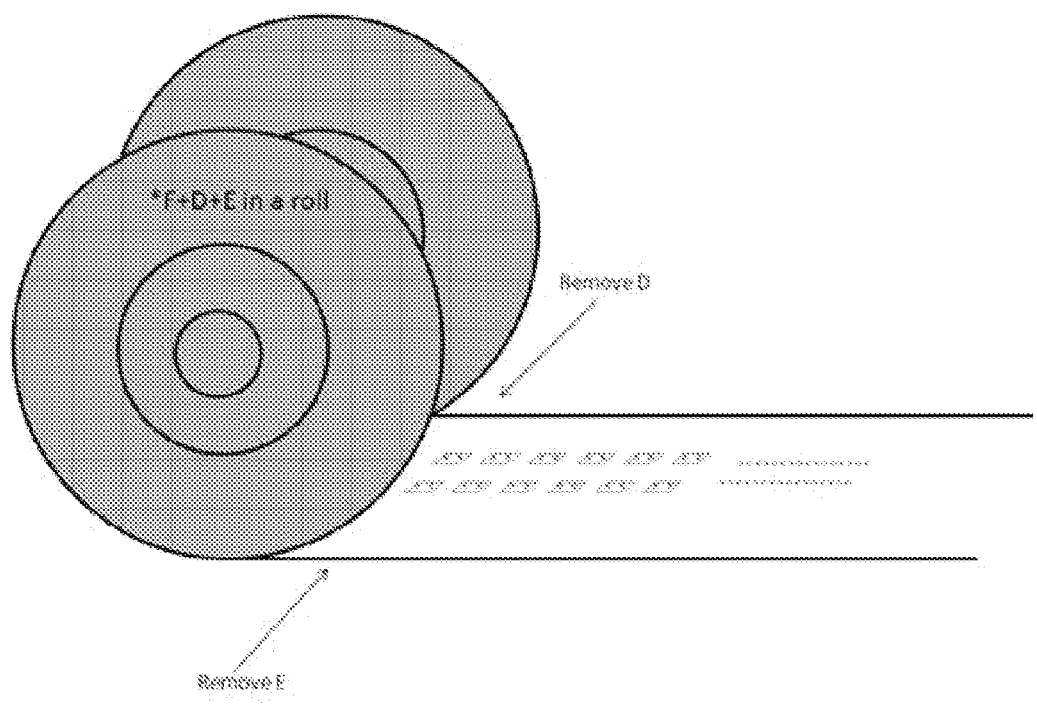
FIG. 9 depicts an aspect of an exemplary fabrication method according to the invention.

By using a replica molding technique, structures with different gap sizes can be fabricated, which can provide sample concentration-specific chambers. The unique fabrication method can be incorporated into a manufacture regime, such that the slides are made with 2 protective films on top and bottom (FIG. 7). Furthermore, tracking holes can be used to advance sheet processed slides similar to that of the analog cameras with advancing films (FIG. 8). Additionally, the slides can be replicated on rolls of plastic, which can further reduce the cost and time of manufacturing (FIG. 9). The counting chambers can be mass-manufactured using rolls of plastic and adhesive, that would significantly reduce the time and cost of the process.

In one aspect, the invention generally relates to a sample chamber suitable for holding a liquid sample for optical imaging. The sample chamber includes: a top layer; an adhesive layer; a bottom layer; a sample holding cavity between the adhesive layer and the bottom layer having a fixed depth of from about 0.5 μm to about 1,000 μm; and an assess port for placing a sample into or out of the chamber; wherein at least a portion of the adhesive layer is optically clear in the range of about 250 nm to about 10,000 nm in wavelength, and wherein at least a portion of the top layer and the bottom layer is optically clear in the range of about 300 nm and about 10,000 nm in wavelength.

The bottom layer of the sample chamber further includes a base film.

In certain embodiments, the sample holding cavity of the sample chamber has a fixed depth of from about 1 μm to about 100 μm. In certain preferred embodiments, the sample holding cavity has a fixed depth of from about 2 μm to about 50 μm. In certain preferred embodiments, the sample holding cavity has a fixed depth of from about 2 μm to about 20 μm. In certain other preferred embodiments, the sample holding cavity has a fixed depth less than about 2 μm. In certain other preferred embodiments, the sample holding cavity has a fixed depth less than about 1 μm.

In some embodiments, at least a portion of the adhesive layer is optically clear in the range of about 300 nm to about 10,000 nm in wavelength, and wherein at least a portion of the top and the bottom layers is optically clear in the range of about 300 nm and about 10,000 nm in wavelength.

The top layer of the sample chamber may be made of a material selected from the group consisting of polyester, polycarbonate, poly(methyl methacrylate) (PMMA), polystyrene and cyclic olefin copolymer, and other optically clear plastic films.

The adhesive layer of the sample chamber may be a pressure-sensitive adhesive layer that includes a material selected from acrylic or acrylate adhesive.

The bottom layer may include an irradiation or thermally cured material. For example, the bottom layer may be a UV-cured polymeric material. In certain preferred embodiments, the UV-cured materials are selected from the group consisting of UV-cured acrylate, urethane and epoxy.

In certain preferred embodiments, the sample chamber further includes a backing layer that is bond to the bottom layer. The backing layer may include a material selected from the group consisting of polyester, polycarbonate, PMMA, polystyrene and cyclic olefin copolymer, and other optically clear plastic films.

In another aspect, the invention generally relates to a sample chamber suitable for holding a biological sample for optical imaging. The sample chamber includes: an optically clear bottom layer; an optically clear top layer; an optically clear adhesive layer binding the top layer on one side and forming a sample holding chamber on the other side with an irradiation- or thermally-cured polymer layer, wherein the sample holding chamber having a fixed depth from the adhesive layer to the irradiation- or thermally-cured polymer layer of from about 0.5 μm to about 1,000 μm; an inlet port for introducing a sample into the chamber; and an outlet port for removing a sample from the chamber (the sample holding cavity).

In some embodiments, the sample holding chamber has a fixed depth of from about 1 μm to about 100 μm. In certain preferred embodiments, the sample holding chamber has a fixed depth of from about 2 μm to about 50 μm. In certain preferred embodiments, the sample holding chamber has a fixed depth of from about 2 μm to about 20 μm. In certain other preferred embodiments, the sample holding chamber has a fixed depth of less than about 2 μm. In certain other preferred embodiments, the sample holding chamber has a fixed depth of less than about 1 μm.

For some applications, it is preferred that at least a portion of the adhesive layer is optically clear in the range of about 250 nm to about 10,000 nm in wavelength.

The top layer may be made of a material selected from the group consisting of polyester, polycarbonate, PMMA, polystyrene and cyclic olefin copolymer.

The adhesive layer may be a pressure-sensitive adhesive layer comprising a material selected from acrylic or acrylate adhesive.

The bottom layer may include an irradiation or thermally cured material. In certain preferred embodiments, the bottom layer comprises a UV-cured polymeric material, for example, a material selected from the group consisting of acrylate, urethane and epoxy.

In certain preferred embodiments, the sample chamber further includes a backing layer that is bond to the bottom layer. The backing layer may be made of a material selected from the group consisting of polyester, polycarbonate, PMMA, polystyrene and cyclic olefin copolymer.

In yet another aspect, the invention generally relates to a method for fabricating a sample chamber. The method includes: providing an optically clear backing layer; placing uniformly an irradiation- or thermally-curable layer on the backing layer; imprinting a preformed structure mold on to the irradiation- or thermally-curable layer, wherein the preformed structured mold protruding into the irradiation- or thermal-curable layer; curing the irradiation- or thermally-curable layer by irradiation or thermal treatment; removing the preformed structure mold, thereby forming an imprinted structure in the irradiation- or thermal-cured layer reflecting the preformed structure of the mold; and placing an optically clear top film having an optically clear adhesive layer on to the imprinted structure of the irradiation- or thermally-cured layer, thereby forming a chamber having the imprinted structure.

The method may further include: forming one or more access port on the chamber allowing introduction and removal of a sample.

The optically clear backing layer is made of a material selected from the group consisting of polyester, polycarbonate, PMMA, polystyrene and cyclic olefin copolymer.

The irradiation layer may be made of an UV-curable material selected from the group consisting of UV-cured acrylate, urethane and epoxy.

The optically clear top film is made of a material selected from the group consisting of polyester, polycarbonate, PMMA, polystyrene and cyclic olefin copolymer.

In some preferred embodiments, the preformed structure mold is formed from aluminum mold.

In some embodiments, an adhesive is coated onto the top layer (e.g., film) for support, and the top layer and the adhesive layer together are directly applied onto the structured surface of the bottom layer to make the chamber.

In yet another aspect, the invention generally relates to a method for manufacturing a sample chamber suitable for holding a biological sample. The method includes: imprinting a preformed structure mold on to an irradiation- or thermal-curable layer, the preformed structured mold protruding into the irradiation- or thermal-curable layer; curing the irradiation- or thermal-curable layer to form an optically clear layer thereby forming a chamber having the imprinted structure; removing the preformed structure mold; binding an optically clear top film to the imprinted structure of the irradiation- or thermal-cured layer, thereby forming a sample chamber; and forming one or more access port on the chamber allowing introduction and removal of a sample.

A desired structure can be formed by thermal casting (e.g., directly on the bottom layer by casting a melting plastic onto a mold surface to form the bottom part. A desired structure can be formed by thermal stamping (e.g., to thermal stamp a plastic film to form the structure). These processes only involve employ heat to "shape" a plastic material to form the needed structures on the plastic material and no chemical reaction is needed. The invention also relates to sample chambers wherein the bottom layer is formed by thermal casting or thermal stamping.

Thus, in yet another aspect, the invention generally relates to a method for manufacturing a sample chamber suitable for holding a biological sample. The method includes: imprinting a preformed structure mold on to a melt plastic layer; cooling the melt plastic layer resulting an imprinted structure thereon; removing the preformed structure mold; binding an optically clear top film to the imprinted structure, thereby forming a sample chamber; and forming one or more access port on the chamber allowing introduction and removal of a sample.

In yet another aspect, the invention generally relates to a method for manufacturing a sample chamber suitable for holding a biological sample. The method includes: stamping a hot preformed structure mold on to a plastic layer, resulting an imprinted structure thereon; removing the preformed structure mold; cooling the plastic layer; binding an optically clear top film to the imprinted structure, thereby forming a sample chamber; and forming one or more access port on the chamber allowing introduction and removal of a sample.

Samples that may be analyzed using the methods of the invention include biological materials obtained from or derived from living organisms. Typically the sample will include bacteria, parasites, cells, tissues, or biomolecules, such as proteins, polynucleotides (e.g., DNA or RNA), organic material, and any combination of the foregoing. Such samples include, but are not limited to, hair, skin, tissue, cultured cells, cultured cell media, and body fluids.

A tissue is a mass of connected cells and/or extracellular matrix material, e.g., CNS tissue, neural tissue, eye tissue, liver tissue, placental tissue, mammary gland tissue, gastrointestinal tissue, musculoskeletal tissue, genitourinary tissue, and the like, derived from, for example, a human or other mammal and includes the connecting material and the liquid material in association with the cells and/or tissues. A body fluid is a liquid material derived from, for example, a human or other mammal. Such body fluids include, but are not limited to, blood, plasma, serum, serum derivatives, bile, phlegm, saliva, sweat, amniotic fluid, mammary fluid, and cerebrospinal fluid (CSF), such as lumbar or ventricular CSF. A sample also may be media containing cells or biological material.

Systems of the invention can also be used to interrogate cell lines. Cell lines refer to specific cells that can grow indefinitely given the appropriate medium and conditions. Systems of the invention can be used to interrogate any type of cell line. Cell lines can be mammalian cell lines, insect cell lines or plant cell lines. Exemplary cell lines can include tumor cell lines or stem cell lines.

EXAMPLES

An aluminum mold was placed on a 30 mil PC (polycarbonate) sheet with the green liner removed. Then, a solution of a UV-curable polymer was pipetted on to the surface of the aluminum mold with approximately 5 large drops across the entire surface. A 30 mil (a "mil" is $1,000^{th}$ of an inch) PC sheet (cut into 4 pieces) was then placed on top of the aluminum mold and the UV-curable solution was allowed to spread across the surface. The entire set was cured in a UV chamber for about 12-15 seconds. The top 30 mil PC sheet was removed with the structure of the chambers imprinted on the surface. A standard top sheet of a Nexcelom counting slide (Model No. CHT4-PD, CHT4-SD) was cut out and bottom liner removed. An optically clear transfer adhesive was placed on the bottom of the top slide sheet. Two holes were punched to form the fluidic inlet and outlet ports. The bottom liner of the transfer adhesive was removed and rolled on to the cured imprinted structure with a metal roller to prevent adhesive from touching down to the surface. Finally, the extra plastic area was cut off.

Figure 10:
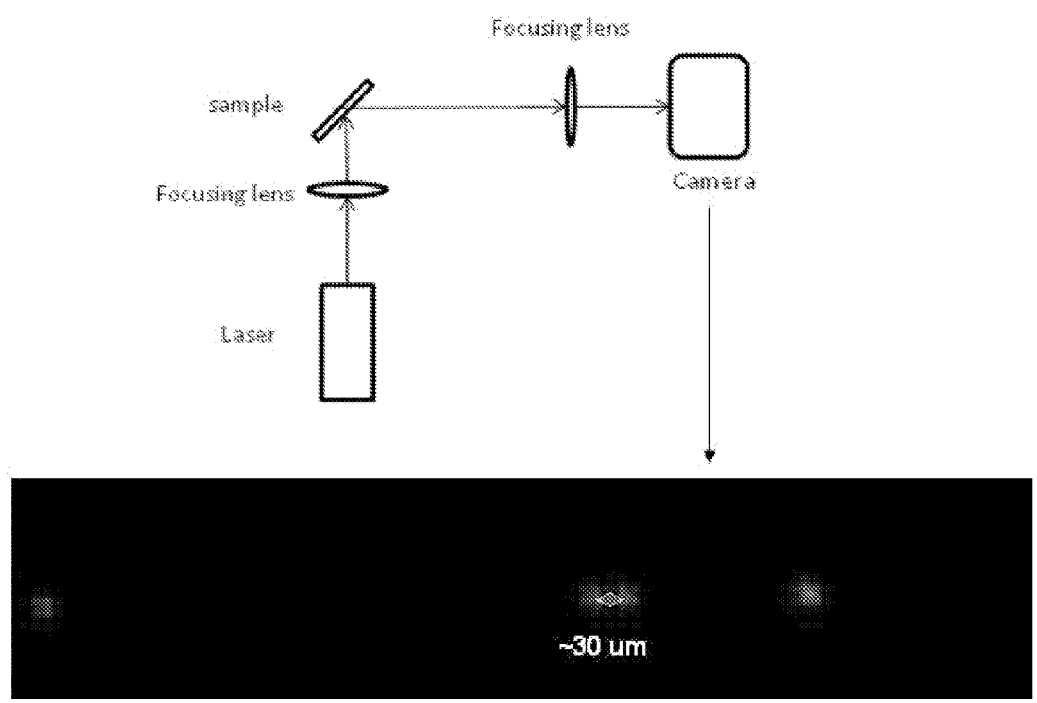
FIG. 10 depicts an illustration of an exemplary laser distance measurement setup and an exemplary image obtained.

Several parameters were tested. First, the size of the gap in the chamber was measured using a home-built laser position detector which measured the reflection of light from each layer of the slide (see FIG. 10). The measured distance was used to calculate the gap size. Secondly, fluorescence from 2.5 µm beads within the chamber was measured to test the fluorescence capability of the slides and the auto fluorescence from the optical adhesive. Thirdly, a well-collimated illuminating light source was used in order to prevent a bright center in the image. Finally, fluidic flow characteristics in thin gap chambers were found to meet the requirements.

Figure 11:
FIG. 11 depicts an exemplary thin gap chamber slide according to an embodiment of the invention.
Figure 12:
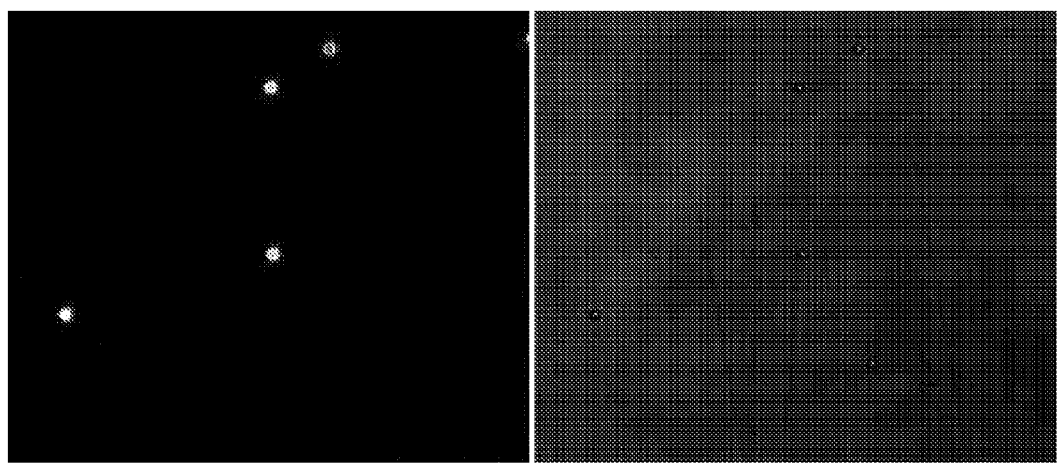
FIG. 12 depicts an exemplary fluorescence of 2.5 µm beads using an exemplary thin gap chamber slide according to an embodiment of the invention.
Figure 13:
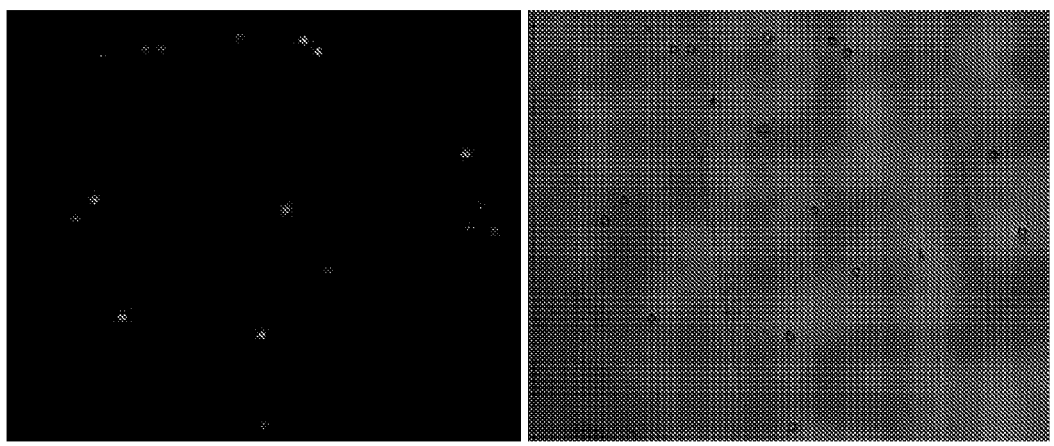
FIG. 13 depicts an exemplary fluorescence of 2.5 µm beads using an exemplary thin gap chamber slide according to an embodiment of the invention.
Figure 14:
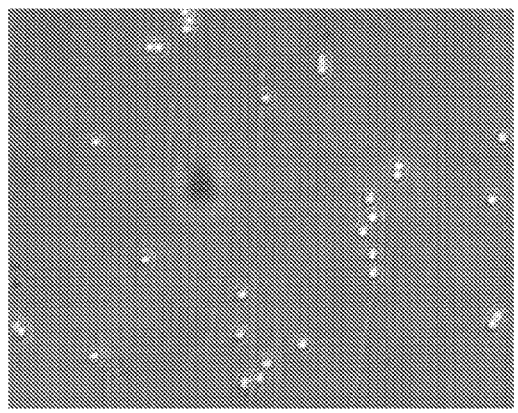
FIG. 14 depicts an exemplary bright field and fluorescence of 2.5 µm beads using an exemplary thin gap chamber slide according to an embodiment of the invention.
Figure 14:
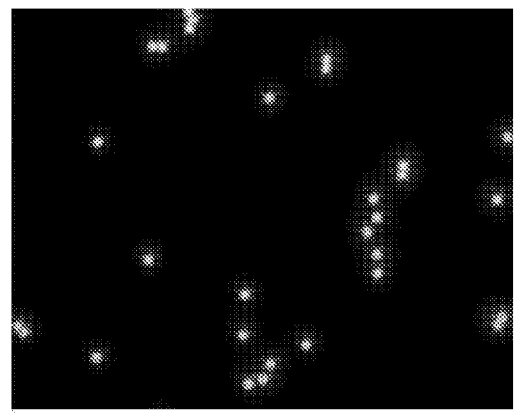

The thin gap chamber slide is shown in FIG. 11. The gap size using the laser position detector measured approximately 30 µm depth. The laser position detector used a 532 nm green laser that is focused on to the chamber. The reflection of light at different layer produced a bright light, which was used to estimate the chamber depth. The fluorescence of 2.5 µm beads (linearFlow, Invitrogen) in the thin gap chamber was observed for both green and orange emission fluorescence channel. FIG. 12 shows the bright field (right) and fluorescence image (left) of the 2.5 µm beads in a thin gap chamber for green emission. FIG. 13 shows the bright field (right) and fluorescence image (left) of the 2.5 µm beads in a thin gap chamber for orange emission. FIG. 14 shows the bright field (right) and fluorescence image (left) of the 2.5 µm beads in a thin gap chamber for blue emission.

Figure 15:
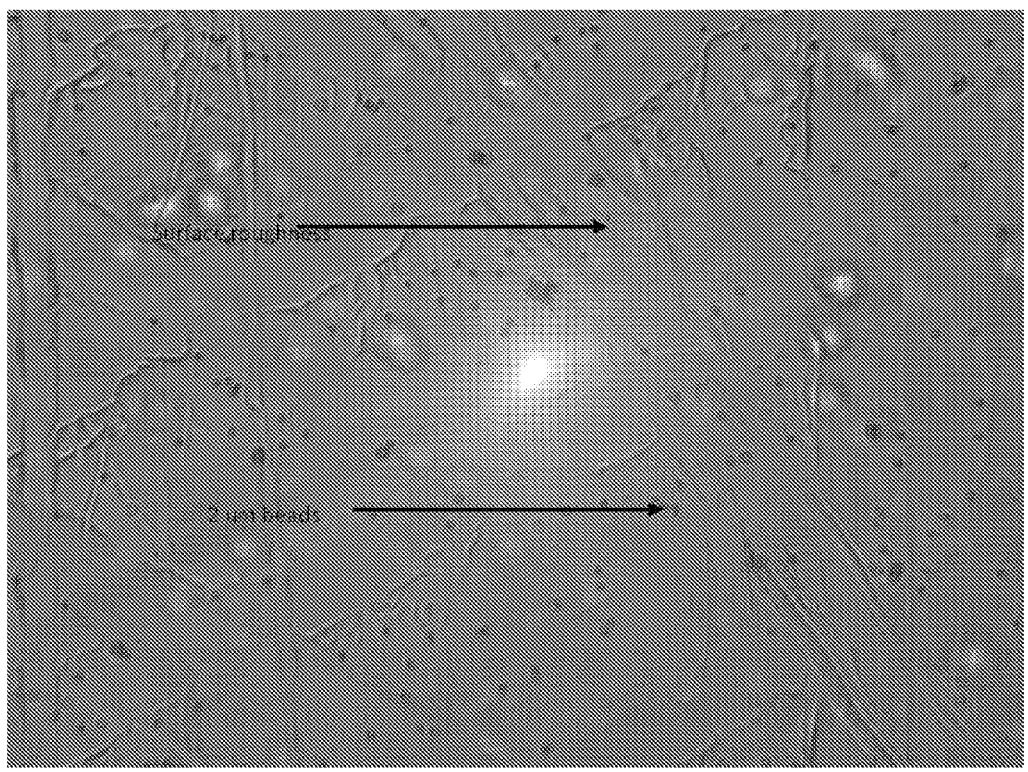
FIG. 15 depicts an exemplary of bright field image of 2 µm beads using an exemplary thin gap chamber slide according to an embodiment of the invention.

In another example, 2 µm beads were used. In order to improve the flow of solution into the chamber, 2.5, 5, 10, and 20% IPA (isopropyl alcohol) solution was mixed with the 2 µm beads, which enhanced the flow speed dramatically from greater than 5 min to less than 5 seconds (approximately 4, 3, 2, and 1 second for 2.5, 5, 10, and 20% IPA, respectively). FIG. 15 shows the bright field image of 2 µm beads in a fabricated thin gap chamber, to show the dispersion of beads inside the chamber. The beads were observed to continuously flow for a long period of time before settling down. By taping both outlet and inlet ports with scotch tape, the settle time were reduced from about 15 min to less than about 5 min. The temperature gradient from the light did not affect the flow of beads.

Figure 16:
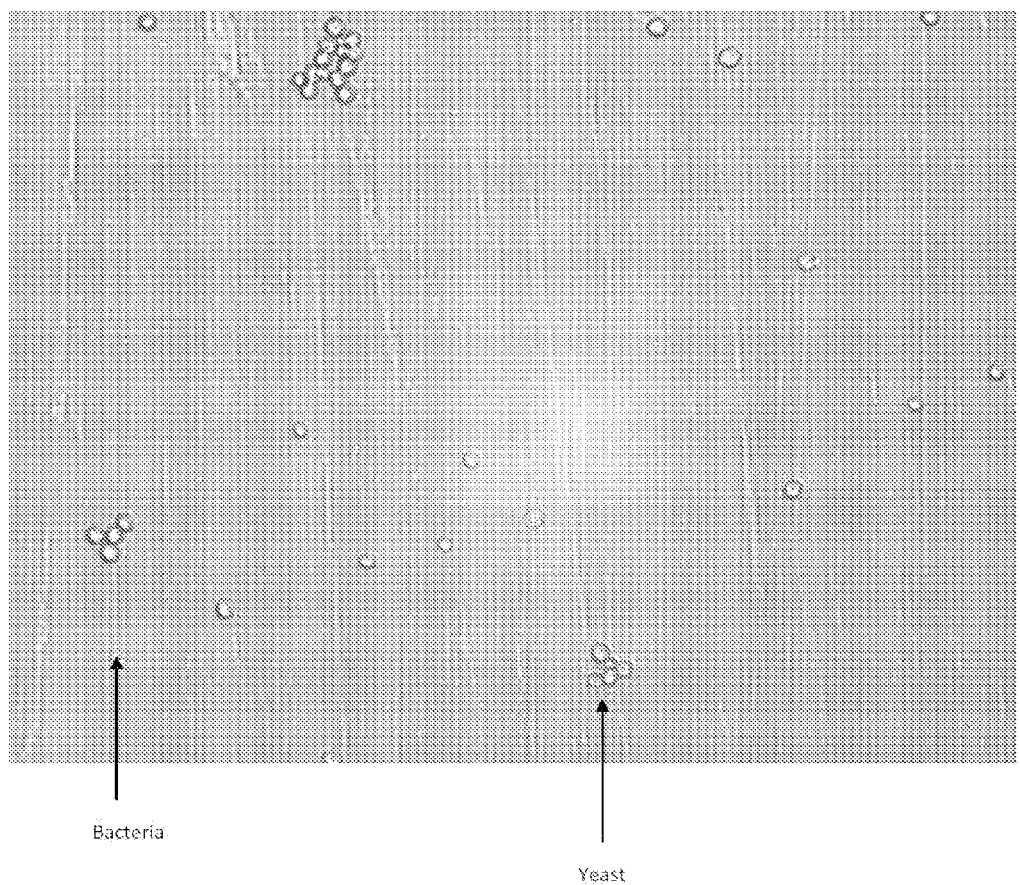
FIG. 16 depicts an exemplary of bright field image of yeasts and bacteria using an exemplary thin gap chamber slide according to an embodiment of the invention.
Figure 17:
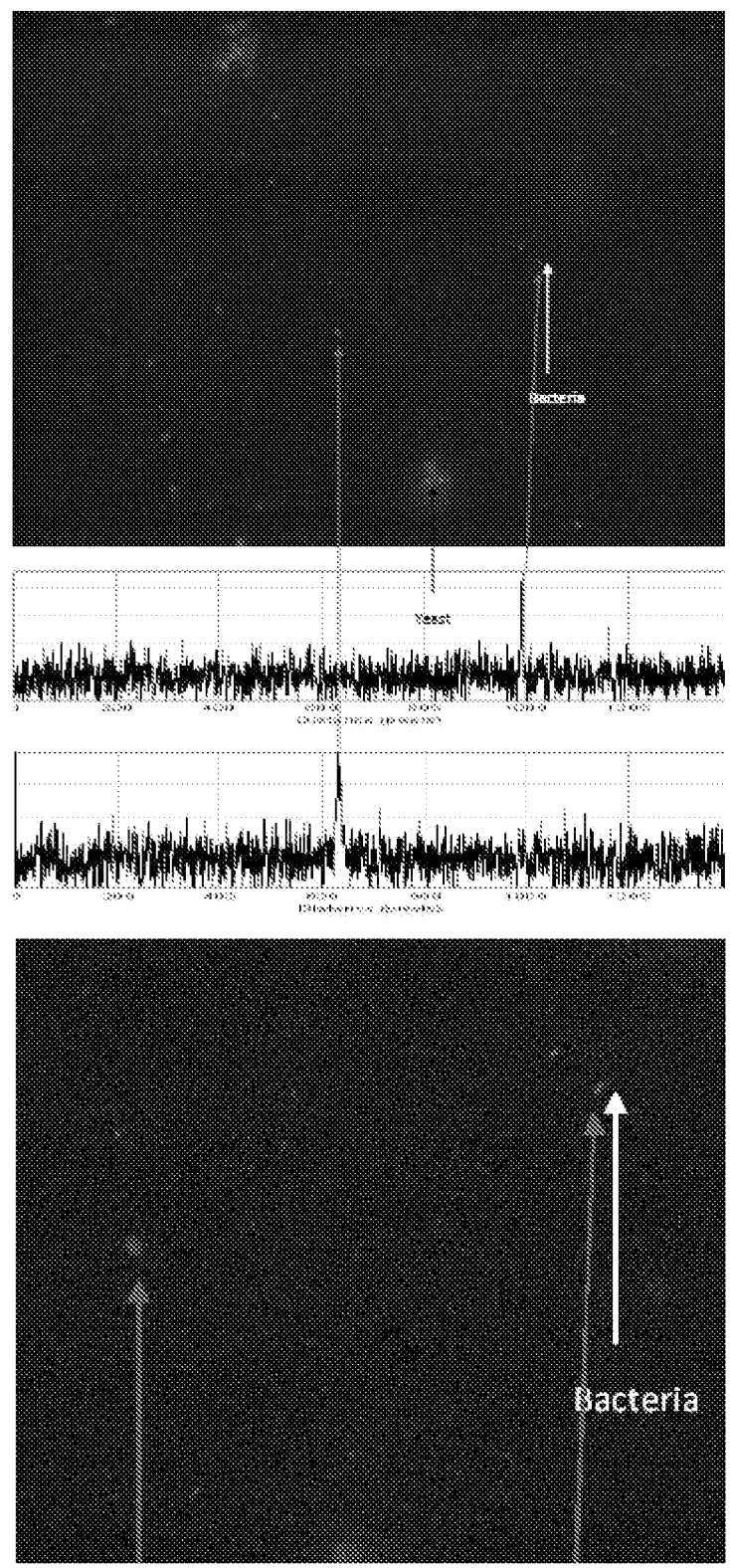
FIG. 17 depicts an exemplary of fluorescence image of yeast and bacteria using an exemplary thin gap chamber slide according to an embodiment of the invention with the signal size presented in a cross section of the image.
Figure 18:
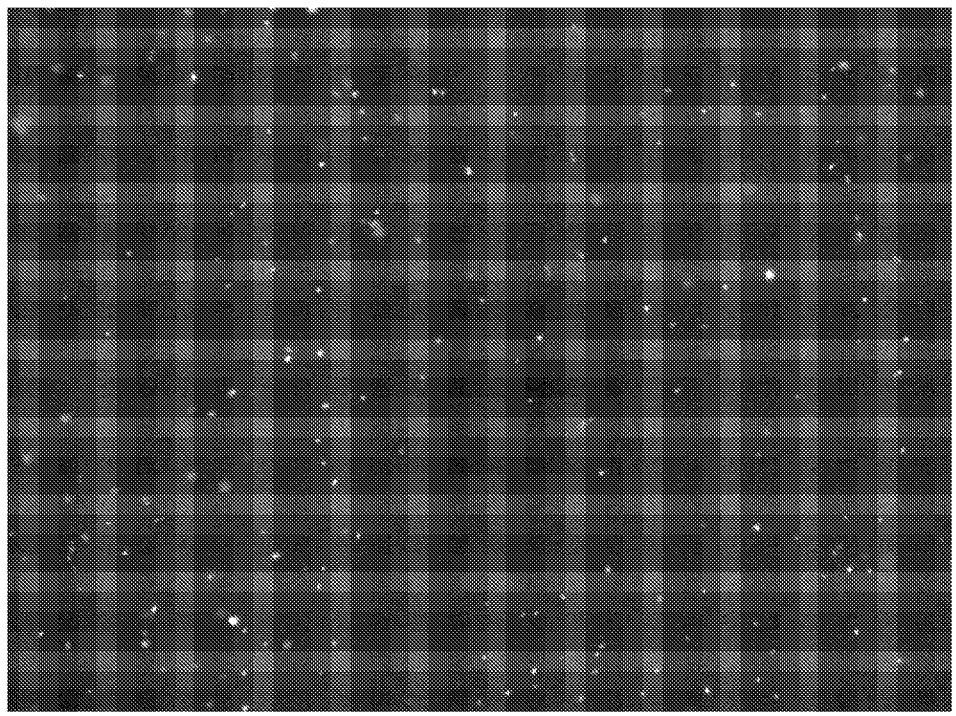
FIG. 18 depicts an exemplary of fluorescence image of yeast and bacteria using an exemplary thin gap chamber slide according to an embodiment of the invention and stained with SYTO9 (Invitrogen) instead of Acridine Orange.

Yeast and bacteria samples were imaged (FIGS. 16-18) and the results demonstrate the effectiveness of the cell chamber and methods of the invention. In FIG. 16, by utilizing 20× objective and thin gap chamber, yeasts and yogurt bacteria were simultaneously observed in the bright field image. The yeasts and bacteria sample was stained with Acridine Orange (AO), which is a nuclear stain that stains all cells. The fluorescence image of yeasts and bacteria is shown in FIG. 17, and the signals are shown in a cross section of the image. Furthermore, other dyes such as SYTO9 (Invitrogen) may be used to perform the same staining quality as AO (FIG. 18).

Incorporation by Reference

References and citations to other documents, such as patents, patent applications, patent publications, journals, books, papers, web contents, have been made in this disclosure. All such documents are hereby incorporated herein by reference in their entirety for all purposes.

Equivalents

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance which can be adapted to the practice of this invention in its various embodiments and equivalents thereof.

What is claimed is:

1. A sample chamber suitable for holding a liquid sample for optical imaging, comprising:
    a top layer;
    an adhesive layer;
    a bottom layer;
    a sample holding cavity between and defined by the adhesive layer and the bottom layer having a fixed depth of from about 1 µm to about 100 µm;
    an inlet port having an opening in the top layer for placing a liquid sample into the chamber; and
    an outlet port having an opening in the top layer for removing the liquid sample out of the chamber;
wherein at least a portion of the adhesive layer is optically clear in the range of about 250 nm to about 10,000 nm in wavelength, and wherein at least a portion of the top layer and the bottom layer is optically clear in the range of about 300 nm and about 10,000 nm in wavelength.

2. The sample chamber of claim 1, wherein the bottom layer comprises a base film.

3. The sample chamber of claim 1, wherein the top layer comprises a material selected from the group consisting of polyester, polycarbonate, PMMA, polystyrene and cyclic olefin copolymer.

4. The sample chamber of claim 1, wherein the adhesive layer is a pressure-sensitive adhesive layer comprising a material selected from acrylic or acrylate adhesive.

5. The sample chamber of claim 1, wherein the bottom layer comprises an irradiation or thermally cured material.

6. The sample chamber of claim 5, wherein the bottom layer is an irradiation cured material.

7. The sample chamber of claim 6, wherein the bottom layer is a UV-cured material.

8. The sample chamber of claim 7, wherein the UV-cured materials is selected from the group consisting of UV-cured acrylate, urethane and epoxy.

9. The sample chamber of claim 1, further comprising a backing layer bond to the bottom layer.

10. A sample chamber suitable for holding a biological sample for optical imaging, comprising:
    an optically clear bottom layer;
    an optically clear top layer;
    an optically clear adhesive layer binding the top layer on one side and forming a sample holding chamber on the other side with an irradiation or thermally cured polymer layer, wherein the sample holding chamber having a fixed depth, as defined by the depth from the adhesive layer to the irradiation- or thermally-cured polymer layer, of from about 1 µm to about 100 µm;
    a first opening in the optically clear top layer for introducing the sample into the chamber; and
    a second opening in the optically clear top layer for removing the sample from the chamber.

11. The sample chamber of claim 10, wherein the optically adhesive layer is wherein at least a portion of the adhesive layer is optically clear in the range of about 250 nm to about 10,000 nm in wavelength.

12. The sample chamber of claim 10, wherein the top layer comprises a material selected from the group consisting of polyester, polycarbonate, PMMA, polystyrene and cyclic olefin copolymer.

13. The sample chamber of claim 10, wherein the adhesive layer is a pressure-sensitive adhesive layer comprising a material selected from acrylic or acrylate adhesive.

14. The sample chamber of claim 10, wherein the bottom layer comprises an irradiation or thermally cured material.

* * * * *